US010105245B2

(12) United States Patent
Ondersma et al.

(10) Patent No.: US 10,105,245 B2
(45) Date of Patent: Oct. 23, 2018

(54) STENT GRAFT ASSEMBLY FOR TREATING BRANCHED VESSELS

(71) Applicant: Cook Medical Technologies LLC, Bloomington, IN (US)

(72) Inventors: Joel Ondersma, Bloomington, IN (US); James A. Teague, Spencer, IN (US); Johnny LeBlanc, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 420 days.

(21) Appl. No.: 13/974,321

(22) Filed: Aug. 23, 2013

(65) Prior Publication Data

US 2015/0057737 A1 Feb. 26, 2015

(51) Int. Cl.
*A61F 2/856* (2013.01)
*A61F 2/852* (2013.01)
(Continued)

(52) U.S. Cl.
CPC .............. *A61F 2/856* (2013.01); *A61F 2/07* (2013.01); *A61F 2/852* (2013.01); *A61F 2/954* (2013.01);
(Continued)

(58) Field of Classification Search
CPC .......... A61F 2/852; A61F 2/856; A61F 2/954; A61F 2250/006; A61F 2250/0063;
(Continued)

(56) References Cited

U.S. PATENT DOCUMENTS 5,824,040 A * 10/1998 Cox .......................... A61F 2/07
606/194
6,645,242 B1 * 11/2003 Quinn ...................... A61F 2/07
623/1.13
(Continued)

FOREIGN PATENT DOCUMENTS

EP 2837362 A1 2/2015
WO WO 03/082153 A2 10/2003
(Continued)

OTHER PUBLICATIONS

Extended European Search Report dated Aug. 28, 2015 for corresponding EP 14275175, 6 pages.

*Primary Examiner* — Ryan J Severson
*Assistant Examiner* — Charles Wei
(74) *Attorney, Agent, or Firm* — Brinks Gilson & Lione

(57) ABSTRACT

This invention relates generally to an endoluminal prosthesis, and more particularly, to a stent graft assembly and method for treating branched vessels. The assembly includes a first prosthesis, such as an iliac branch device (IBD), comprising a tubular main body, a first leg extending from a distal end of the main body and at least one fenestration formed in the main body. An internal tubular side branch extends proximally from the fenestration into the lumen of the main body, resulting in an iliac branch device having an overall reduced proximal length. The assembly further includes a second prosthesis, or a bridging limb, having a distal end with a scalloped fenestration formed therein to accommodate sealing with the proximal end of the iliac branch device without interfering with the internal branch. A connecting stent graft adapted for placement in the internal iliac artery may be sealingly connected to the internal branch.

18 Claims, 4 Drawing Sheets

(51) Int. Cl.
*A61F 2/07* (2013.01)
*A61F 2/954* (2013.01)
*A61F 2/06* (2013.01)

(52) U.S. Cl.
CPC ... *A61F 2002/061* (2013.01); *A61F 2002/067* (2013.01); *A61F 2002/075* (2013.01); *A61F 2220/0075* (2013.01); *A61F 2250/006* (2013.01); *A61F 2250/0039* (2013.01); *A61F 2250/0063* (2013.01)

(58) Field of Classification Search
CPC A61F 2002/067; A61F 2/04–2002/077; A61F 2/82–2/945
USPC .................................................. 623/1.13, 1.16
See application file for complete search history.

(56) References Cited

U.S. PATENT DOCUMENTS

| | | | | |
|---|---|---|---|---|
| 6,814,752 B1* | 11/2004 | Chuter | ...................... | A61F 2/07 623/1.27 |
| 7,407,509 B2 | 8/2008 | Greenberg et al. | | |
| 7,435,253 B1 | 10/2008 | Hartley et al. | | |
| 2002/0099436 A1* | 7/2002 | Thornton | ................. | A61F 2/06 623/1.12 |
| 2002/0198587 A1* | 12/2002 | Greenberg | ................ | A61F 2/07 623/1.13 |
| 2003/0074055 A1* | 4/2003 | Haverkost | ................ | A61F 2/07 623/1.16 |
| 2003/0199967 A1* | 10/2003 | Hartley | ..................... | A61F 2/07 623/1.13 |
| 2004/0082990 A1* | 4/2004 | Hartley | ..................... | A61F 2/07 623/1.13 |
| 2004/0117003 A1* | 6/2004 | Ouriel | ....................... | A61F 2/07 623/1.35 |
| 2009/0138072 A1* | 5/2009 | Gendreau | ............. | A61B 50/30 623/1.15 |
| 2011/0190868 A1* | 8/2011 | Ducke | ....................... | A61F 2/07 623/1.13 |
| 2013/0211505 A1* | 8/2013 | Robison | ..................... | A61F 2/07 623/1.35 |

FOREIGN PATENT DOCUMENTS

WO  WO 2006/028925 A1  3/2006
WO  WO 2006/113501 A1  10/2006

\* cited by examiner

STENT GRAFT ASSEMBLY FOR TREATING BRANCHED VESSELS

BACKGROUND

This invention relates generally to medical devices, and more particularly, to endoluminal prostheses such as stent grafts and methods for treating branched vessels. The functional vessels of human and animal bodies, such as blood vessels and ducts, occasionally weaken or even rupture. For example, a vessel wall can weaken, resulting in an aneurysm, or it may develop a tear in one of the layers of the wall resulting in a dissection.

One common surgical intervention for weakened, aneurysmal or ruptured passageways or ducts involves the use of an endoluminal prosthesis to provide some or all of the functionality of the original, healthy passageway or duct and/or preserve any remaining vascular integrity by replacing a length of the existing passageway or duct wall that spans the site of failure or defect. Endoluminal prostheses may be of a unitary construction or may be comprised of multiple prosthetic segments. They also may be a single tubular device or a bifurcated branching device depending on the desired application or the particular portion of the vasculature being treated.

In many cases, the damaged or defective portion of the vasculature may include a branch vessel extending from a main vessel. Fenestrated and/or branched endoluminal prostheses are known for treating such branch vessels. In one example, an iliac branch device (IBD) may be placed in the common iliac artery (CIA). An iliac branch device generally consists of a main lumen which runs from the CIA to the external iliac artery (EIA) with a side branch extending from the main lumen and facing the internal iliac artery (IIA). The proximal end of the iliac branch device may connect directly to an AAA main body graft, or alternatively, the proximal end of the iliac branch device may be sealed to the AAA main body via an intermediate bridging limb.

Introduction of an iliac branch device and successful deployment thereof may often depend upon a favorable layout of the arteries. However, the anatomy of the vasculature may be unique from one patient population to the next and also among individual patients. Anatomical limitations may restrict the patient base which is able to receive a branched graft, such as an iliac branch device, the chief limitation being the length of the common iliac artery. In one example, branched stent grafts have been used to treat patients having common iliac arteries of a certain average length (e.g., the measured distance from the main aortic bifurcation to the ostium of the internal iliac artery), such as approximately 40 mm in length or greater. The common iliac artery must be of a certain minimum length in order for the iliac branch device to seat properly, such that the fenestration and/or side branch of the graft is adjacent the ostium of the IIA while the proximal end of the iliac branch device does not extend above the aortic bifurcation, for example. However, the length of the common iliac arteries among certain patient populations, particularly in Asia, may be on average shorter, down to 20 mm in length or even less, such that treatment with a standard length iliac branch device may be difficult.

SUMMARY

A stent graft assembly is disclosed which accommodates the vasculature of diverse patient populations having unique layouts and varying geometries, including, but not limited to, patients having shorter than average length common iliac arteries. The disclosed stent graft assembly includes an iliac branch device having an internal branch facing the IIA, resulting in a reduced overall proximal length (measured from a proximal end of the iliac branch device to the furthest distal extent of the fenestration or side branch). The assembly further includes a scalloped bridging limb which accommodates sealing with the proximal end of the iliac branch device without interfering with the internal branch and/or flow therethrough.

In one example, the stent graft assembly comprises a first prosthesis comprising a tubular main body formed of biocompatible graft material having a proximal end portion, a distal end portion and lumen extending therebetween, a first leg extending from the distal end portion of the main body, at least one fenestration formed in the tubular main body and an internal tubular branch extending proximally from the at least one fenestration into the lumen of the main body. The assembly further comprises a second prosthesis comprising a tubular body of biocompatible graft material having a proximal end portion and a distal end portion and a scalloped fenestration formed in the graft material at the distal end portion. The distal end portion of the second prosthesis is configured to sealingly engage the proximal end portion of the main body of the first prosthesis and the scalloped fenestration is aligned with the internal tubular branch when the first and second prostheses are sealingly engaged.

A method for treating a diseased vessel is described. The method comprises the steps of introducing a delivery device carrying a first prosthesis into a patient's vasculature, the first prosthesis comprising a tubular main body formed of biocompatible graft material having a proximal end portion, a distal end portion and lumen extending therebetween, a first leg extending from the distal end portion of the main body, at least one fenestration formed in the tubular main body and an internal tubular branch extending proximally from the at least one fenestration into the lumen of the main body. The method further comprises positioning the first prosthesis in the patient's vasculature such that the main body is located in the common iliac artery, the first leg is located in the external iliac artery and the at least one fenestration is directed towards an internal iliac artery of the common iliac artery and at least partially deploying the first prosthesis in the patient's vasculature. A second prosthesis is then introduced into the patient's vasculature, the second prosthesis comprising a tubular body of biocompatible graft material having a proximal end portion and a distal end portion and a scalloped fenestration formed in the graft material at the distal end portion. The scalloped fenestration is aligned with the internal side arm and the proximal end portion of the first prosthesis is sealingly connected with the distal end of the second prosthesis.

DETAILED DESCRIPTION

Throughout this specification, the terms proximal and proximally are used for a position or direction towards the patient's heart and the terms distal and distally are used for a position or direction away the patient's heart. The embodiments described below are in connection with the deployment of an implantable medical device, such as an endoluminal prosthesis, including, but not limited to stents, stent grafts, occlusion devices and the like. The term "branch vessel" refers to a vessel that branches off from a main vessel. Examples are the celiac and renal arteries which are branch vessels to the aorta, the aorta being the main vessel in this context. As another example, the internal iliac is a branch vessel to the common iliac, the common iliac being the main vessel in this context. Thus, the terms "branch vessel" and "main vessel" are relative terms.

Figure 1A:
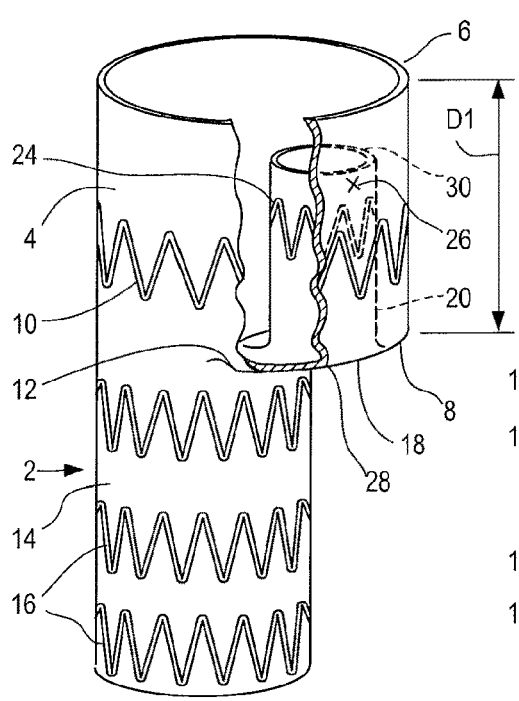
FIG. 1a shows one example of a branched stent graft having a fully internal branch.

Referring now to FIG. 1a, an exemplary prosthesis such as a stent graft is shown generally at 2. In one example, the stent graft is configured for deployment in the iliac arteries and may be referred to herein as an "iliac branch device" or IBD. The graft 2 preferably includes a tubular main body portion 4 of biocompatible polymeric graft material having a proximal end 6 and a distal end 8. The main tubular body portion is preferably adapted for placement in the common iliac artery (CIA) for example, but it is also contemplated that the main body portion 4 may be placed in other arteries or vessels. The tubular main body portion 4 may have a diameter ranging from about 14 mm to about 24 mm. One or more stents 10 may be sutured, or otherwise attached, to the outside of the main body portion 4 near the proximal end 6. Further stents may be positioned below the stent 10, and may be sutured, or otherwise attached, to the inside and/or the outside of the main body portion 4.

Extending from the main body 4 at a bifurcation 12 is a tubular first leg 14. The first leg 14 may be adapted for placement in the external iliac artery (EIA) for example, and may have a diameter ranging from about 8 mm to about 16 min. One or more stents 16 may be sutured, or otherwise attached, to the inside and/or the outside of the first leg 14. The placement of the stents 10, 16 at the upper and lower ends of the prosthesis 2 provides stability as well as a good sealing surface where the prosthesis 2 can engage the wall of the vessel lumen into which the prosthesis is inserted. The stents 10, 16 attached to the main body portion 4 and/or the leg 14 may be standard z-stents such as Gianturco Z stents, spiral-z stents, rings or a combination thereof, and may be constructed from various known materials such as Nitinol, stainless steel, and/or other suitable materials.

As shown in FIG. 1a, adjacent to the leg 14 and at the bifurcation 12 is an opening 18. Extending up into the main body 4 from the opening 18 is a cylindrical tubular portion or internal branch 20 which extends proximally some distance up into the lumen of main body 4. The internal branch 20 may have a diameter in the range of about 6 mm to about 12 mm, thus providing a socket for receiving and sealingly engaging a connection stent graft 22 (see FIGS. 3 and 4, for example) as will be described in further detail below. The internal branch is intended to remain inside the lumen of the main body 4.

Figure 1B:
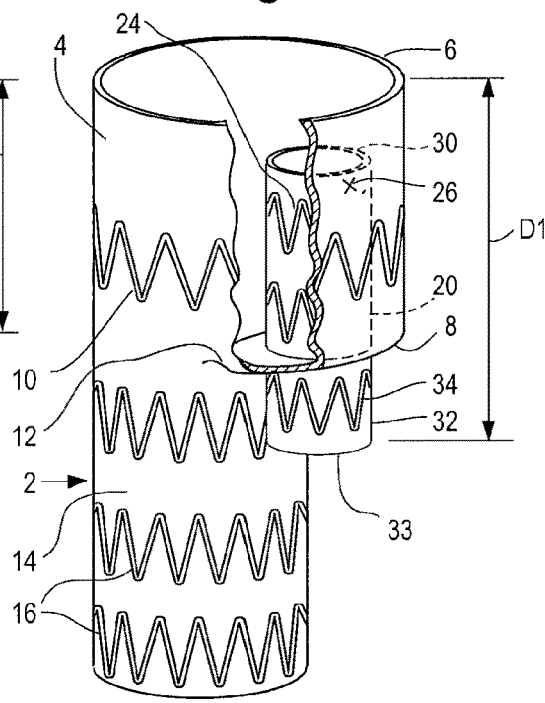
FIG. 1b shows an alternative example of a branched stent graft having an internal branch with a partial externally extending portion.

The internal branch 20 may have at least one stent 24 on its outside and/or its inside surface, or both surfaces, which stent(s) 24 may have any one of the previously described geometries. FIG. 1a illustrates one stent 24 on the outside of the internal branch 20 while FIG. 1b illustrates two stents 24 on the outside surface of the internal branch 20. Alternatively, the internal branch 20 may be completely unsupported.

The internal branch 20 may be constructed in several different ways. In one example, the internal branch 20 could be produced by inverting an external side branch extending from aperture 18 in a proximal direction into the aperture 18 so that the branch extends proximally inside the lumen of main body 4. One or more attachment mechanisms may be provided, such as suture or stitch 26 near the proximal end 30 of the internal branch 20 and/or near distal fold 28 (not shown) such that the internal branch 20 cannot slide or become displaced. Alternatively, the internal branch 20 may also be constructed from a separate piece of tubular graft material which can then be sewn into place in the lumen of the main body portion 4 just proximal to and about the fenestration aperture 18 at bifurcation 12. The graft material of the internal branch 20 may be sutured to the wall of the main graft body 4 at one or more points proximal of the aperture 18 to hold the tube in place as previously described, such as with stitch(es) 26 near the proximal end 30 and/or near distal end 28 of the internal branch 20.

In another embodiment, as shown in FIG. 1b, the internal branch 20 may have a short segment 32 protruding external to the main body 4 and extending distally from the fenestration 18. The proximal end 30 of the internal branch 20 extending proximally into the main body 4 lumen may include one or more stents 24 sewn or otherwise attached on its internal and/or external surface, while the short segment 32 protruding distally from the opening 18 may also include one or more stents 34 sewn or otherwise attached, to either the inside or outside surface of the graft material. The stents 24, 34 may have any one of the previously described geometries.

Figure 3:
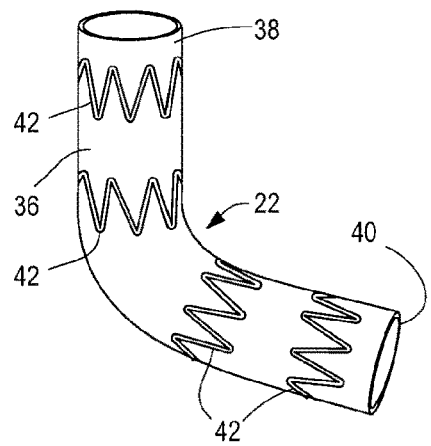
FIG. 3 illustrates one example of a connection stent graft adapted for sealing engagement with the internal branch of the branched stent graft shown FIGS. 1a and 1b.
Figure 4:
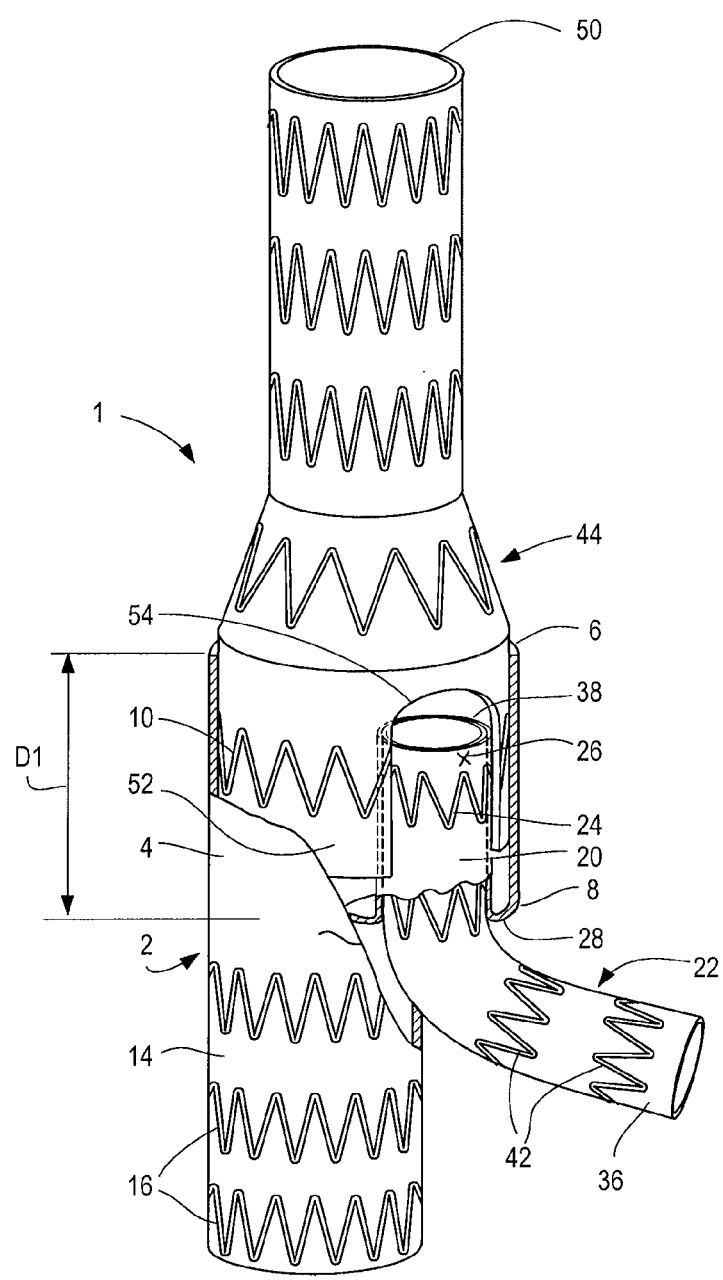
FIG. 4 shows one example of an assembly including the bridging limb shown in FIG. 2 sealingly connected to the proximal end of the branched stent graft shown in FIG. 1a and a connection stent illustrated in FIG. 3 sealingly connected to the assembly.
Figure 5:
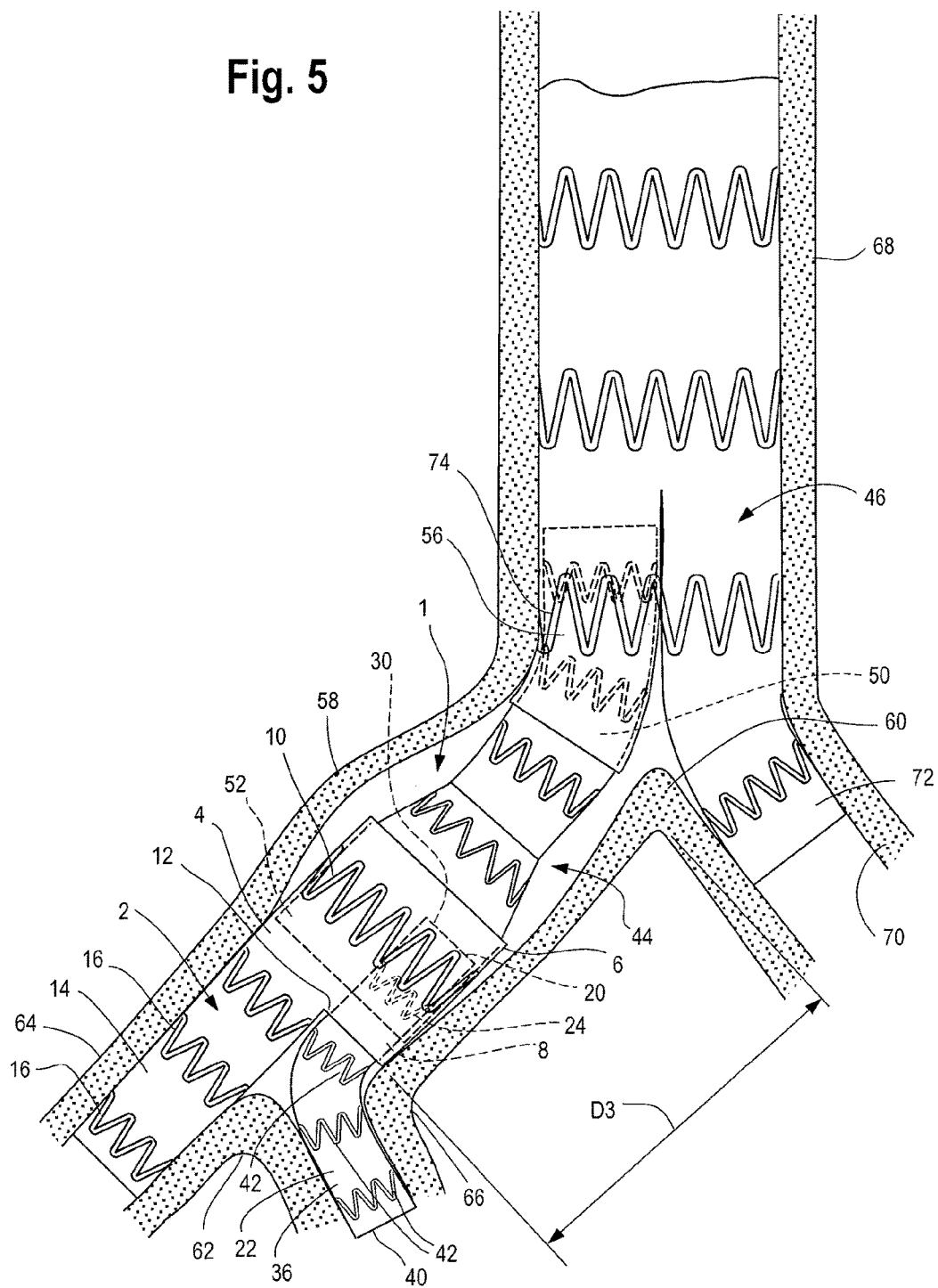
FIG. 5 shows one example of the assembly of FIG. 4 placed in the vasculature of a patient and spanning an aneurysm in the common iliac artery.

As shown in FIGS. 4 and 5, a connection stent graft 22, as shown in FIG. 3, may be placed such that it extends distally from the internal branch 20, preferably into the internal iliac artery. As shown in detail in FIG. 3, the connection stent graft 22 preferably comprises a substantially tubular body 36 having a proximal end 38 and a distal end 40. The proximal end 38 of the connection stent graft 22 may sealingly engage with the internal branch 20. The overlap between the internal surface of the side branch 20 and external surface of the connection stent graft 22 at its proximal end 38 provides a secure connection therebetween. One or more stents 42 may be sutured, or otherwise attached, to the inside and/or the outside of the connection stent graft 22 between its proximal 38 and distal ends 40. In one example, the connection stent graft 22 can be a covered balloon expandable stent or a covered self-expanding stent, with the stents having one or more of the previously described shapes and constructions.

As previously mentioned, the disclosed branched stent graft 2 increases the patient base able to receive endovascular treatment therewith, due, in one respect, to the overall reduced length of the iliac branch device. The reduction in overall length of the iliac branch device is, in one example, achieved by the internal branch. More specifically, connection stent grafts 22 such as that described above may typically require 10-18 mm of overlap between the proximal end 38 of the connection stent graft 22 and a side branch of the iliac branch device. Previously, this overlap has been achieved by extending the side branch externally from a fenestration in the iliac branch device. An external side branch, however, increases the overall length of the iliac branch device such that the iliac branch device may no longer be suitable for patients having anatomical limitations including shortened CIAs.

By extending the internal branch 20 proximally and internally within the lumen of the main body 4 of the iliac branch device 2 (as opposed to an external side branch), the overall length of the device 2 can be reduced or minimized without sacrificing the overlap length needed to secure the proximal 38 end of the connection stent graft 22 and the internal branch 20. As such, the connection stent graft 22 may be securely, sealingly connected to the iliac branch device 2 within the "socket" provided by the internal branch 20.

Figure 2:
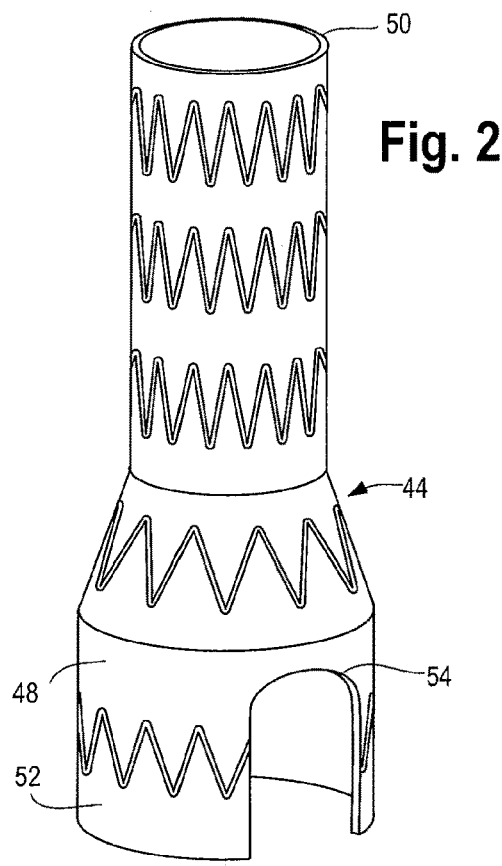
FIG. 2 illustrates one example of a bridging limb having a scalloped fenestration.

Turning now to FIGS. 4 and 5, the proximal end 6 of the iliac branch device 2 is preferably connected to a second prosthesis 44 (shown in FIG. 2). In one example, the second prosthesis is a bridging limb 44. The iliac branch device 2 and the bridging limb 44 together form the disclosed assembly 1 shown in FIG. 4. As FIG. 5 illustrates, the iliac branch device 2 is in fluid communication to a proximally located third prosthesis, such as an AAA bifurcated stent graft 46, (i.e., a Zenith AAA stent graft; Cook Incorporated, Bloomington, Ind.) via the intermediate bridging limb 44. The bridging limb 44 preferably comprises a tubular body 48 of biocompatible graft material having a proximal end 50 and a distal end 52 and a lumen extending therebetween. The distal end 52 of the bridging limb 44 may include at least one scalloped fenestration 54 formed in the graft material. The bridging limb 44 may be a provided in a variety of shapes, lengths and sizes. For example, the bridging limb 44 may preferably be provided in a range of lengths such that it can adequately bridge the distance between iliac branch device 2 and the AAA stent graft 46.

As shown in FIGS. 4 and 5, the internal branch 20 extends proximally within the main body 4 such that the proximal end 30 of the internal branch 20 terminates at or near the proximal end 6 of the main body 4 of the iliac branch device 2. In other words, the proximal end 30 of the internal branch 22 may overlap with the portion of the main body 4 that seals with the bridging limb 44. Accordingly, a scalloped fenestration 54 formed in the distal end 52 of the bridging limb 44 is preferably configured to accommodate sealing with the proximal end 6 of the iliac branch device 2 without interfering with the internal branch 20. The scalloped fenestration 54 may be generally U-shaped and opens to the distal end 52 of the bridging limb 44. However, it is also contemplated that the scalloped fenestration 54 can have other shapes or configurations, and preferably, has a geometry that corresponds generally to that of the internal branch 20 as described below. Reinforcing material may be provided around the periphery of the scalloped fenestration 54 to give good dimensional stability to the fenestration as described in further detail in U.S. Published application 2011/0190868, including a wire, a composite wire, and the like, which disclosure is incorporated by reference herein in its entirety.

In one example, as shown in FIG. 4, the scalloped fenestration 54 and the internal branch 20 are aligned and correspondingly shaped such that the scalloped fenestration 54 can arch over the proximal end 30 of the internal branch 22. The scallop 54 may be oversized to allow for some alignment inaccuracy, or alternatively, the scallop 54 could be sized to fit snugly over the internal branch 20. During deployment of the stent graft assembly 1 described herein, alignment of the scallop 54 with the internal branch 20 allows the bridging limb 44 to expand at its distal end 52 to sealingly connect to the proximal end 6 of the iliac branch device 2 without closing off flow to the internal branch 20 or to the connection stent graft 22 extending from the internal branch 20 into the internal iliac artery.

Figure 6:
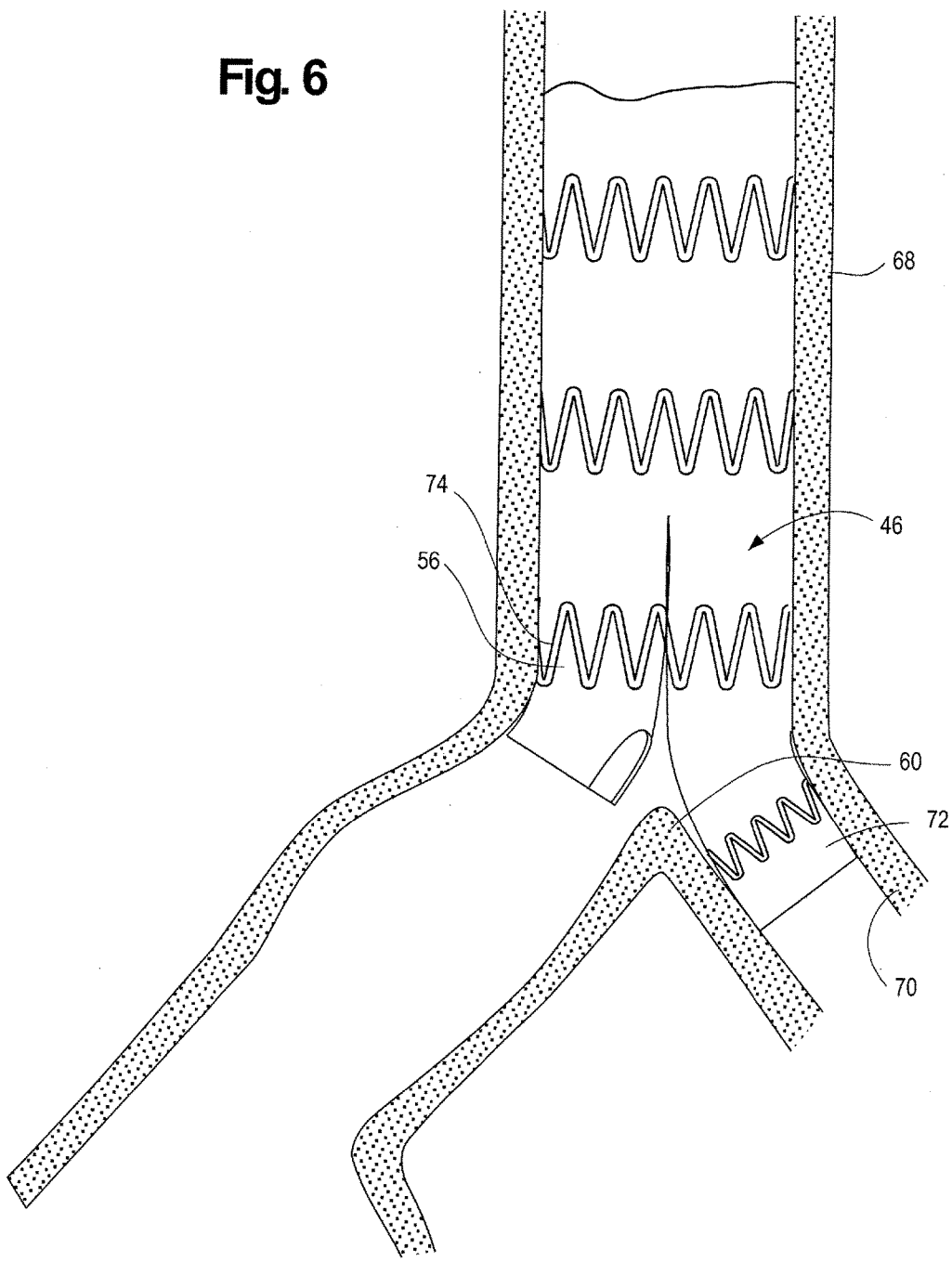
FIG. 6 shows an alternative example of a scalloped stent graft.

In an alternative example, the proximal end 6 of the iliac branch device 2 may be connected directly to a distal end 56 of the AAA bifurcated graft 46 (thereby eliminating the intermediate bridging limb 44). In such case as shown in FIG. 6, the distal end 56 of the AAA graft 46 preferably comprises a scalloped fenestration 54 like that described above in relation to the bridging limb 44, which is designed to accommodate the internal branch 20 of the iliac branch device 2 and to provide a sealing connection between the iliac branch device 2 and the AAA graft 46 without interfering with flow into the internal branch 20. In such a case where the iliac branch device is connected directly to a distal end of the AAA graft 46, however, it would be preferable that the iliac branch device 2 be sealingly connected to the longer leg 72 of the AAA graft 46 so that the scalloped fenestration 54 is formed in the distal end of the longer leg 72.

An iliac branch device 2 having the above-described features has an overall reduced proximal length, a dimension "D1" that is shown, for example, in FIGS. 1a, 1b and 4, which is the distance measured from a proximal end 6 of the device 2 to the furthest distal extent 8, 33 of the fenestration 18 or side branch 20. As shown in FIG. 5, the assembly 1 may be successfully deployed into an aneurised common iliac artery 58 having a particular length, which is the distance "D3" measured from aortic bifurcation 60 down to the proximal side of the internal iliac ostium. The overall reduced length D1 is preferably less than the distance D3 to allow, for example, cannulation of the internal iliac artery 66 and also to allow the contralateral limb of the AAA graft 46 to open/expand fully to allow it to be cannulated for deployment of the bridging limb 44.

The length of the first leg 14 of the iliac branch device 2 is preferably such that it can extend to non-aneurised region of the external iliac artery 64 so that a seal may be obtained with the distal end of the leg 14. Where the aneurism extends some distance down the external iliac artery 64 a further leg extension (not shown) may be placed so that the stent graft assembly 1 extends through non-aneurised region of the external iliac artery. The above-described assembly 1 can be inserted sequentially into the vasculature, including the common 58, external 64 and internal 66 iliac arteries, to repair one or more aneurysms formed therein.

FIG. 5 shows an example of the assembly 1 comprising an iliac branch device 2, and a proximally located bridging limb 44 seated into an aneurised common iliac artery 58. A connection stent graft 22 is also shown, sealingly engaged with the internal branch 20 at its proximal end 38. The illustrated vasculature generally consists of an aorta 68 extending down to an aortic bifurcation 60 and into the iliac 58 and contra-iliac arteries 70. The common iliac artery 58 further bifurcates at 62 into an external iliac artery 64 and an internal iliac artery 66. The internal iliac artery 66 is a blind artery, as endovascular access is only available via the common iliac artery 58.

The assembly 1 may be deployed using standard endoluminal techniques. For example, one or more components of the assembly may be may be compressed into a delivery configuration and loaded into a delivery device, such as an introducer or sheath and deployed using the devices and/or methods described in U.S. Pat. No. 7,435,253 to Hartley et al. and U.S. Pat. No. 7,407,509 to Greenberg et al., which are incorporated by reference herein in their entireties.

In one non-limiting example, the general order of delivery and placement of such a stent graft assembly 1 for treatment of aneurised iliac arteries may be as follows. First, iliac branch device 2 is placed with the distal end of leg 14 into a non-aneurised region of the external iliac artery 64. The fenestration 18 (or distal end 33 of protruding segment 32 of FIG. 1b) is adjacent to and faces towards the internal iliac artery 66. Subsequent to placement of the iliac branched stent graft 2, a connection stent graft 22, which extends down into the internal iliac artery 66, may be placed. A proximal end portion 38 of the connection stent graft 22 is sealingly engaged within the socket formed by the internal branch 20. The connection stent graft 22 extends from the internal branch 20 distally into, and seals in, the internal iliac artery 66. The distal end 40 of the connection stent graft 22 engages in a sealing manner into a non-aneurysed portion of the internal iliac artery 66.

If necessary or desired to treat an aneurised portion of the aorta, a main AAA bifurcated stent graft 46, such as the Zenith AAA stent graft (Cook Incorporated, Bloomington, Ind.) may be deployed through the contra-lateral iliac artery 70 so that its longer leg 72 extends down the contra-lateral iliac artery 70 and its shorter leg 74 terminates proximal of the proximal end 6 of the iliac branch device 2 and proximal of the aortic bifurcation 60. A second prosthesis, such as a bridging limb 44 described above having a scalloped fenestration at its distal end shaped to align with and accommodate the internal branch, may then be deployed to connect the shorter leg 74 of the main bifurcated AAA stent graft 46 to the proximal end 6 of the iliac branch device 2. Alternatively, the proximal end 6 of the iliac branch device 2 can be connected directly to a distal end of the AAA stent graft 46, and preferably, to a distal end of the longer leg 72 of the AAA stent graft. The AAA stent graft 46 could be deployed through the ipsilateral iliac artery (i.e. the same artery in which the iliac branch device 2 has been placed) and, the distal end of the longer leg 72 would therefore preferably include a scalloped fenestration 54 as described previously to accommodate the internal branch 20 of the iliac branch device 2 and allow expansion of the longer leg 72 without interfering with the internal branch 20.

By this arrangement a stent graft assembly 1, either alone or in combination with a proximally located AAA stent graft 46 and/or a connection stent graft 22 extending into the internal iliac artery, is effectively bridging the aneurised regions of the iliac arteries by sealing in the non-aneurised portion of the vasculature.

It is noted that while the present disclosure generally describes the stent graft assembly 1 in the context of delivery and deployment into the iliac arteries, it is also contemplated that the disclosed assembly in method is also suitable for use in other portions of the vasculature. In one non-limiting example, the assembly may be configured for placement in the aorta and branch vessels extending therefrom such as the brachiocephalic, carotid and/or subclavian arteries. More specifically, the main tubular body 4 of graft 2 may be positioned within the aortic arch. The bridging limb 44 may be sealingly connected to the proximal end 6 of the main tubular body, as illustrated in FIG. 4. The bridging limb may be tapered at its proximal end 50 as shown in FIG. 4, or, alternatively, it may have a substantially constant diameter between the proximal end 50 and distal end 52.

In one example, when the main body 4 is positioned within the aorta, opening 18 is preferably located near the greater curve of the aortic arch adjacent the ostium of one or more of the previously mentioned branch vessels extending from the aorta such that when connection stent graft 22 is sealingly connected within the socket provided by the internal branch 20, the connection stent graft 22 may extend into a branch vessel extending from the aorta (i.e., brachiocephalic, carotid and/or subclavian arteries). It is also contemplated that the main body 4 of graft 2 may also include additional openings or fenestrations 18, with an internal branch 20 extending therefrom within the main body 4, for one or more additional connection stent grafts 22 to extend therefrom so as to provide flow to more than one branch vessel extending from the aorta simultaneously when the main body is positioned within the aorta.

Throughout this specification, unless the context requires otherwise, the words "comprise" and "include" and variations such as "comprising" and "including" will be understood to imply the inclusion of an item or group of items, but not the exclusion of any other item or group items.

While various examples of the invention have been described, it will be apparent to those of ordinary skill in the art that many more examples and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A stent graft assembly comprising:
   i. a first prosthesis comprising a tubular main body formed of biocompatible graft material having a proximal end portion, a proximal end opening, a distal end portion, a lumen extending therebetween, a length and a constant diameter;
   ii. a first leg extending from the distal end portion of the main body;
   iii. at least one fenestration formed in the tubular main body;
   iv. an internal branch extending proximally from the at least one fenestration into the lumen of the main body, the internal branch having a length and a proximal end opening that is open toward the proximal end portion of the main body;
   b. a second prosthesis comprising a tubular body of biocompatible graft material having a proximal end portion and a distal end portion and a scalloped fenestration formed in the graft material at the distal end portion, the scalloped fenestration having a perimeter; and, the prosthesis proximal end portion having a first constant diameter, the distal end portion having a second constant diameter greater than the first constant diameter and a length, and a tapered portion tapering continuously from the first constant diameter to the second constant diameter and having a stent disposed about the taper, wherein the scalloped fenestration extends substantially the entire length of the distal end portion to adjacent the tapered portion;
   c. wherein the distal end portion of the second prosthesis is configured to sealingly engage the proximal end portion of the main body within the lumen of the main body of the first prosthesis and wherein the proximal end portion of the second prosthesis extends beyond the proximal end opening of the main body and the scalloped fenestration perimeter at least partially surrounds the length of the internal branch and arches over the proximal end opening of the internal branch when the first and second prostheses are sealingly engaged; and d. wherein the length of the distal end portion of the second prosthesis is substantially the same as the length of the proximal end portion of the first prosthesis.

2. The assembly of claim 1 wherein the internal branch and scalloped fenestration are correspondingly shaped such that the scalloped fenestration is configured to receive at least a portion of the internal branch.

3. The assembly of claim 1 wherein the scalloped fenestration is configured to fit over the internal branch.

4. The assembly of claim 1 wherein the second prosthesis further comprises a first pre-deployment constricted configuration and a second deployed expanded configuration.

5. The assembly of claim 4 wherein the scallop is configured to bridge the internal branch such that expansion of the second prosthesis does not interfere with the internal branch.

6. The assembly of claim 1 wherein the first prosthesis is configured to be deployed into the vasculature of a patient with the main body being located in the common iliac artery, the first leg being located in the external iliac artery and the at least one fenestration being adjacent to the opening of an internal iliac artery extending from the common iliac artery.

7. The assembly of claim 1 wherein the internal branch provides a socket for a connection stent graft to sealingly connect to the first prosthesis.

8. The assembly of claim 7 wherein the connection stent graft is adapted for placement in an internal iliac artery.

9. The assembly of claim 1 wherein the internal branch is located completely inside the lumen of the main body.

10. The assembly of claim 1 wherein the internal branch comprises a proximal end and a distal end and wherein a portion of the distal end protrudes distally from the fenestration and external to the main body.

11. The assembly of claim 1 wherein the internal branch is integrally formed with the main body of the first prosthesis.

12. The assembly of claim 1 wherein the internal tubular side branch is formed from a separate piece of graft material and secured inside the lumen of the main body of the first prosthesis.

13. The assembly of claim 1 wherein the second prosthesis comprises a bridging limb located proximal to the first prosthesis and distal to a third prosthesis.

14. The assembly of claim 13 wherein the third prosthesis comprises a bifurcated AAA stent graft.

15. The assembly of claim 14 wherein the AAA stent graft and the first prosthesis are in fluid communication via the bridging limb.

16. The assembly of claim 1 wherein the second prosthesis comprises a bifurcated AAA stent graft.

17. A method for treating a diseased vessel, the method comprising:

i. introducing a delivery device carrying a first prosthesis into a patient's vasculature, the first prosthesis comprising a tubular main body formed of biocompatible graft material having a proximal end portion having a length, a proximal end, a distal end portion and lumen extending therebetween;

ii. a first leg extending from the distal end portion of the main body;

iii. at least one fenestration formed in the tubular main body;

iv. an internal tubular branch having a length and extending proximally from the at least one fenestration into the lumen of the main body, the internal branch having a length extending toward the proximal end of the main body and a proximal end opening that is open toward the proximal end of the main body;

b. positioning the first prosthesis in the patient's vasculature such that the main body is located in the common iliac artery, the first leg is located in the external iliac artery and the at least one fenestration is directed towards an internal iliac artery of the common iliac artery;

c. at least partially deploying the first prosthesis in the patient's vasculature;

d. introducing a second prosthesis into the patient's vasculature, the second prosthesis comprising: a tubular body of biocompatible graft material having a proximal end portion, a tapered portion, and a distal end portion having a length and a scalloped fenestration formed in the graft material at the distal end portion and extending for substantially the entire length of the distal end portion, the scalloped fenestration having a perimeter, wherein the distal end portion and the scalloped fenestration of the second prosthesis extend with the lumen of the main body of the first prosthesis and the proximal end portion of the second prosthesis extends beyond the proximal end of the main body, wherein the prosthesis proximal end portion has a first constant diameter, the distal end portion has a second constant diameter greater than the first constant diameter, and wherein the tapered portion tapers continuously from the first constant diameter to the second constant diameter and includes a stent disposed about the taper of the tapered portion, wherein the length of the distal end portion of the second prosthesis is substantially the same as the length of the proximal end portion of the first prosthesis, e. aligning the scalloped fenestration and the internal tubular branch by placing the perimeter of the scalloped fenestration along the length of the internal branch to arch over the proximal end opening of the internal tubular branch; and f. sealingly connecting the proximal end portion of the first prosthesis with the distal end of the second prosthesis.

18. The method of claim 17 further comprising, prior to the step of introducing the second prosthesis;

a. introducing a connection stent graft into the internal iliac artery;

b. sealingly connecting a proximal end portion of the connection stent graft to the internal branch.

* * * * *